United States Patent [19]

Cumbie, Jr.

[11] Patent Number: 4,724,546
[45] Date of Patent: Feb. 16, 1988

[54] VISOR WITH MOVABLE LIGHT SHIELD

[76] Inventor: John K. Cumbie, Jr., 606 Belrose, Daphne, Ala. 36526

[21] Appl. No.: 45,546

[22] Filed: May 4, 1987

[51] Int. Cl.⁴ ............................ A42B 1/24; A61F 9/04
[52] U.S. Cl. ............................................. 2/12; 2/453; 2/432
[58] Field of Search ................... 2/12, 10, 199, 432, 2/453

[56] References Cited

U.S. PATENT DOCUMENTS

| | | | |
|---|---|---|---|
| 1,313,469 | 8/1919 | Crossley | 2/12 X |
| 1,338,022 | 4/1920 | Lamoreaux | 2/12 |
| 1,435,533 | 11/1922 | Knackstedt | 2/12 X |
| 2,146,544 | 2/1939 | Kleine | 2/12 |
| 2,204,688 | 6/1940 | McClung et al. | 2/10 |
| 2,256,966 | 9/1941 | Simonton | 2/12 |
| 2,638,593 | 5/1953 | Eloranta | 2/12 |
| 3,837,005 | 9/1974 | Persson | 2/199 X |
| 4,309,775 | 1/1982 | Jory | 2/432 X |

*Primary Examiner*—Peter Nerbun
*Attorney, Agent, or Firm*—Jennings, Carter, Thompson & Veal

[57] ABSTRACT

A visor assembly utilizes a movable eye screen which passes through a slot in a forwardly extending shade element. The light-transmissive eyescreen is adjustable to a shielding and non-shielding position, where it may be locked in position.

11 Claims, 5 Drawing Figures

VISOR WITH MOVABLE LIGHT SHIELD

FIELD OF THE INVENTION

This invention relates generally to the eyeshields or visors and more particularly to visors with an additional screen element which can be selectively disposed in front of the eyes to reduce the light incident on the eyes.

BACKGROUND OF THE INVENTION

The patent literature discloses numerous attempts in designing a headgear with a sunscreen which can be conveniently positioned relative to the wearer's eyes to provide optimal comfort in varying light environment. It is also known to provide a movable protective screen in combination with a headgear.

U.S. Pat. Nos. 1,313,469; 2,040,614; 2,385,405; and 2,638,593 each show a combination of shade and eyeshield components wherein the eyeshield may be pivoted upwardly to a non-shielding position adjacent the lower surface of the eyeshade. U.S. Pat. Nos. 2,601,149 and 3,721,994 both disclose headgear with a slidable face shield which can be stored within a compartment or housing above the wearer's forehead. U.S. Pat. Nos. 1,610,745; 2,179,719; and 2,968,812 each show headgear with a movable or extendable visor. U.S. Pat. No. 2,256,966 show a combination sunglass and eyeshade.

While each of these are meritorious in their own right, they each leave something to be desired in convenience, reliability, durability, or adaptability. For example: the headgear of U.S Pat. Nos. 2,601,149 and 3,721,994 are hardly suited for beach or recreational wear and the pivotly mounted eyeshields have a tendency to fall from the stored position to the shielding position.

SUMMARY OF THE INVENTION

It is the object of the present invention to provide a combination sunshade and eyescreen which can be easily adjusted to for indoor or outdoor wear without the necessity of removing the sunshade from the head, thereby reducing the annoyance of disturbing the underlying hair or presenting a less than attractive appearance.

Another object of the invention is to provide a combination visor and eyescreen which is lightweight and easily worn.

Yet another object of the invention is to provide a combination visor and eyescreen wherein the eyescreen may be easily secured in a selected position.

BRIEF DESCRIPTION OF THE DRAWINGS

A visor assembly incorporating features of my invention is depicted in the accompanying drawing which form a portion of this invention and wherein.

DESCRIPTION OF A PREFERRED EMBODIMENT

Figure 1:
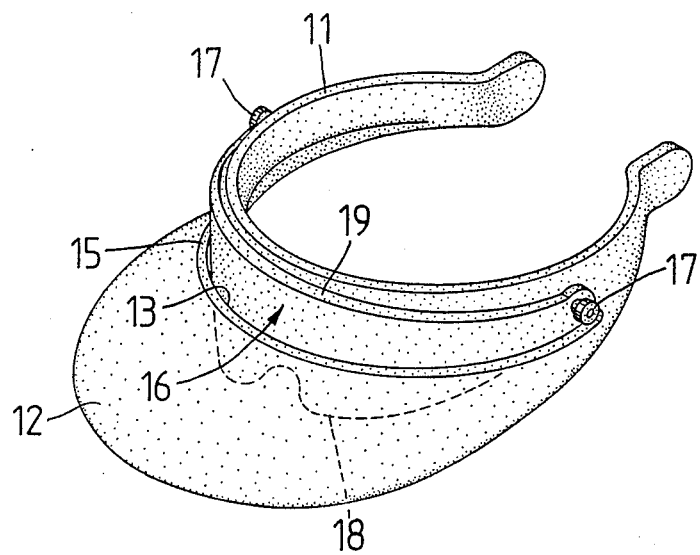
FIG. 1 is a perspective view of my visor and eyeshield combination.
Figure 2:
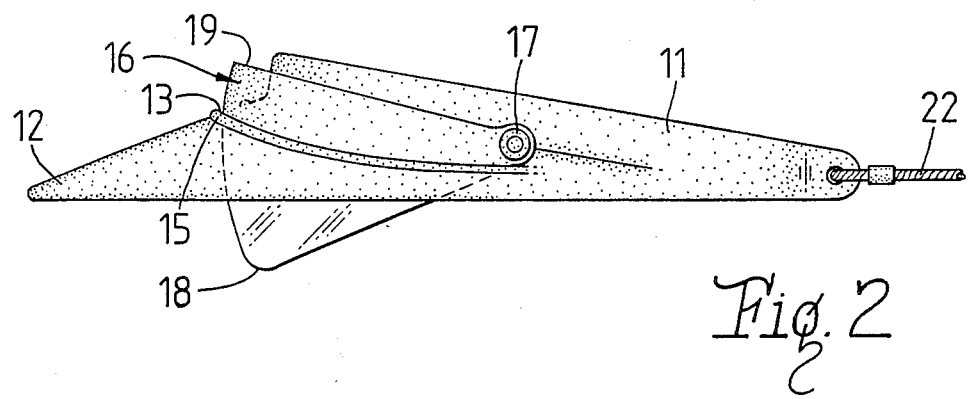
FIG. 2 is a side elevational view of my invention.
Figure 3:
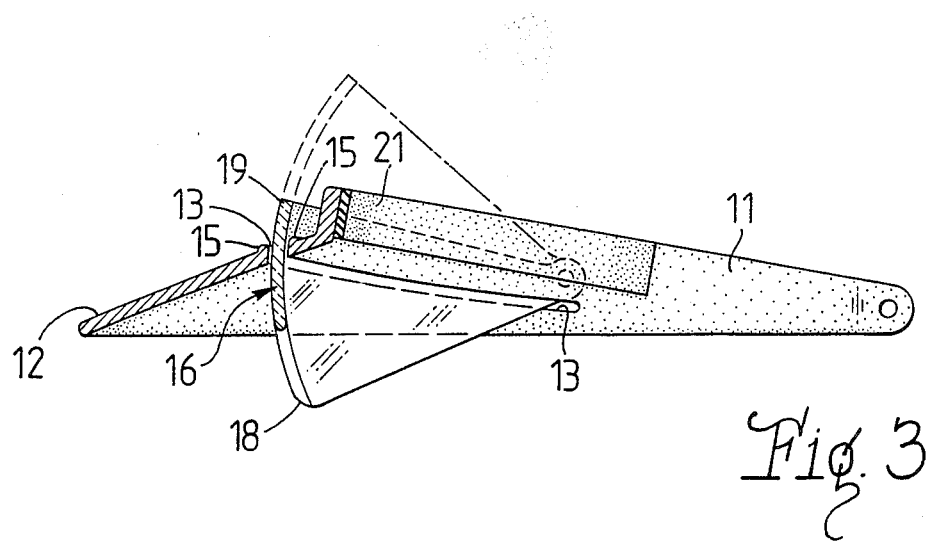
FIG. 3 is a sectional view taken along the centerline of my invention.
Figure 4:
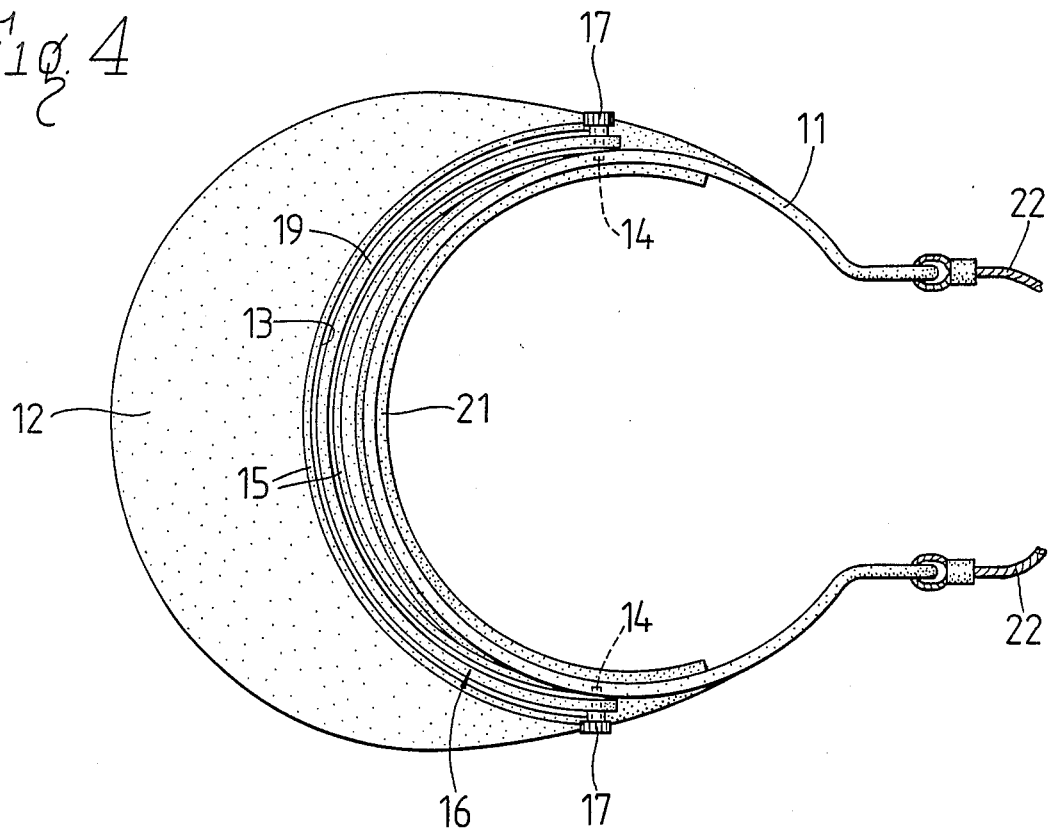
FIG. 4 is a plan view of the visor assembly.
Figure 5:
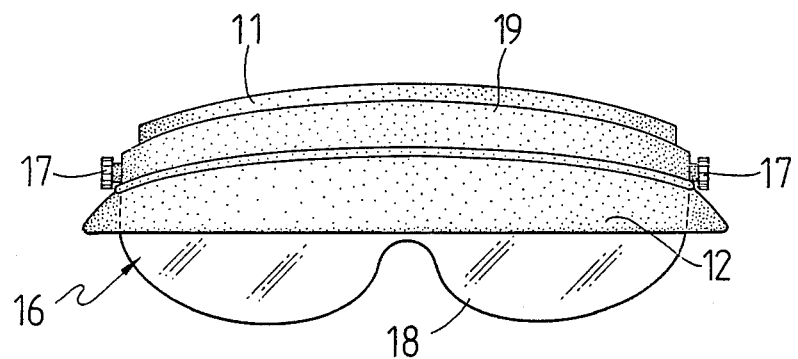
FIG. 5 is a front elevational view of the visor assembly.

As may be seen from FIG. 1, my invention utilizes a head engaging band 11 which may be of the clamp-type as shown or of the head encircling-type as is well known. A bill or shade 12 extends from the band 11 in a conventional manner to provide shade to the region about the eyes. A slot 13 is formed in the shade 12 outwardly of and parallel to the band 11. The slot 13 extends a least the width of the forehead and terminates near a pair of aperture 14 formed in the band 11. The slot 13 is bordered by a bead or rim 15.

A screen 16 is disposed within the slot 13 and attached to the band 11 by a pair of screws 17 threadedly engaging the aperture 14. The screen 16 has a lower edge 18 contoured to conform to the face of the wearer by leaving a slot for the bridge of the nose and being rounded across the cheeks. The screen 16 is essentially a sheet of optically transmissive material which reduces the intensity of the light transmitted therethrough such as is commonly found in sunglass lenses and the like. The upper portion 19 of the screen 16 is preferentially opaque; however, it may be merely painted as with a slogan or advertizing material that would be visible when the screen 16 is covering the eyes of the wearer. Therefore, the upper portion 19 will extend through the slot 13 above the shade 12 at all times. It may be noted that the aperture 14 and slot 13 may be cooperatively positioned such that the edge of the slot 13 closest to the aperture 14 acts as a stop to prevent the screen 16 from decending beyond a desired point thus, preventing the screen 16 from resting on the face of the wearer and maintaining the visibility of the upper portion 19.

The band 11 may be provided with a strip of foam liner 21 and with an auxiliary strap 22. The liner 21 enhances the comfort of the wearer as is conventionally known.

In use, the screws 17 are loosened to permit the screen 16 to be positioned either in a lowered position in front of the eyes or in a raised position above the eyes depending on the amient light conditions. The screws 17 are tightened to hold the screen 16 in place. When it is desired to change the position of the screen 16, the screws 17 can be loosened without removing the visor assembly from the head and the screen 16 can be repositioned. It is preferrable that the band 11 and shade 12 be formed from a resilient plastic and that screws 17 also be made of plastic. It will be appreciated that the inner most ends of the screws 17 can readily be deformed to prevent unintentional disassembly of the screen 16 from the band 11.

The foregoing description has disclosed a unique visor assembly that is comfortable and durable. The unique slotted shade construction allows the screen 16 to pivot yet be retracted from proximal the wearer's face and thus eliminates the screen as a distraction on the underside of the shade 12. Further, by pivoting toward the center of the wearer's head, the center of gravity of the shield 16 is brought closer to the pivot point defined by the pins 17, thus there is no tendency of the visor assembly to be "front heavy" as has been the case in prior art devices wherein the screen pivots upwardly and outwardly to a stored position.

While I have shown my invention in one form, it will be obvious to those skilled in the art that it is not so limited but is susceptible of various changes and modifications without departing from the spirit thereof.

What I claim is:

1. A visor assembly to be worn on a person's head comprising:

(a) headband means engaging the head of the wearer above the eyes and extending at least partially therearound for holding the visor assembly in place;
(b) bill means to said headband means and extending outwardly therefrom for providing shade to an area including the eyes, with said bill means having an elongated slot therethrough extending parallel to said headband means;
(c) movable means for reducing the amount of light transmitted therethrough positioned within said slot and mounted to said headband means for selective movement within said slot to a lowered position in front of the eyes and to a raised position above the eyes wherein said movable means is secured to said headband means by at least one adjustable screw-like member which may be tightened or loosened to lock or unlock said movable means in a selected position.

2. A visor assembly as defined in claim 1 wherein said movable means has a lower edge contoured to cooperate with the face of the wearer.

3. A visor assembly as defined in claim 1 wherein said headband means and said bill means are formed from a resilient plastic material.

4. A visor assembly as defined in claim 1 wherein said movable means include an optically transmissive sheet-like member having an elongated dimension conforming to the length of said slot and being movable vertically within said slot to said lowered and raised positions.

5. A visor assembly as defined in claim 4 wherein said movable means include an optically non-transmissive portion extending above said sheet-like member and said slot when said movable means is in said lowered position.

6. A visor assembly as defined in claim 5 wherein said sheet-like member has a lower edge contoured to cooperate with the face of a wearer when in said lowered position.

7. A visor assembly as defined in claim 1 wherein said bill means has a rib-like projection extending normal thereto about said slot.

8. A visor assembly to be worn on a person's head comprising:
(a) headband means engaging the head of the wearer above the eyes and extending at least partially therearound for holding the visor assembly in place;
(b) bill means secured to headband means and extending outwardly therefrom for providing shade to an area including the eyes, with said bill means having an elongated slot therethrough extending parallel to said headband means;
(c) movable means for reducing the amount of light transmitted therethrough positioned within said slot and mounted to said headband means for selective movement within said slot to a lowered position in front of the eyes and to a raised position above the eyes;
(d) means for selectively locking said movable means in position comprising at least one adjustable screw-like member securing said movable means to said headband means proximal the temples of said wearer.

9. A visor assembly as defined in claim 8 wherein said movable means include an optically transmissive sheet-like member having an elongated dimension conforming to the length of said slot and being movable vertically within said slot to said lowered and raised position.

10. A visor assembly as defined in claim 8 wherein said movable means include an optically non-transmissive portion extending above said sheet-like member and said slot when said movable means is in said lowered position.

11. A visor assembly as defined in claim 8 wherein said sheet-like member has a lower edge contoured to cooperate with the face of a wearer when in said lowered position.

* * * * *